United States Patent
Hu

(10) Patent No.: US 8,609,890 B1
(45) Date of Patent: Dec. 17, 2013

(54) CYCLIC PROCESS FOR THE PRODUCTION OF TAURINE

(76) Inventor: Songzhou Hu, Princeton, NJ (US)

( * ) Notice: Subject to any disclaimer, the term of this patent is extended or adjusted under 35 U.S.C. 154(b) by 0 days.

(21) Appl. No.: 13/573,076

(22) Filed: Aug. 20, 2012

(51) Int. Cl.
*C07C 309/00* (2006.01)

(52) U.S. Cl.
USPC .......................................................... 562/104

(58) Field of Classification Search
None
See application file for complete search history.

(56) References Cited

PUBLICATIONS

SIGMA-ALDRICH specification sheet for technical-grade sulfuric acid.*
SIGMA-ALDRICH product information sheet for technical-grade sulfuric acid.*
Database Caplus Chemical Abstracts Service, Columbus, Ohio, US; Database Accession No. 2009:904671 Abstract of CN 101486669, Guo et al., Jul. 22, 2009.*

* cited by examiner

*Primary Examiner* — Karl J Puttlitz

(57) ABSTRACT

A method is disclosed for the production of taurine by a cyclic process of reacting ethylene oxide with sodium bisulfite and ammonium to obtain sodium taurinate. After excess ammonia is removed from the reaction mixture, sodium taurinate is neutralized with sulfur dioxide or sulfurous acid to recover taurine and to regenerate sodium bisulfate, which is then reacted with ethylene oxide.

3 Claims, 1 Drawing Sheet

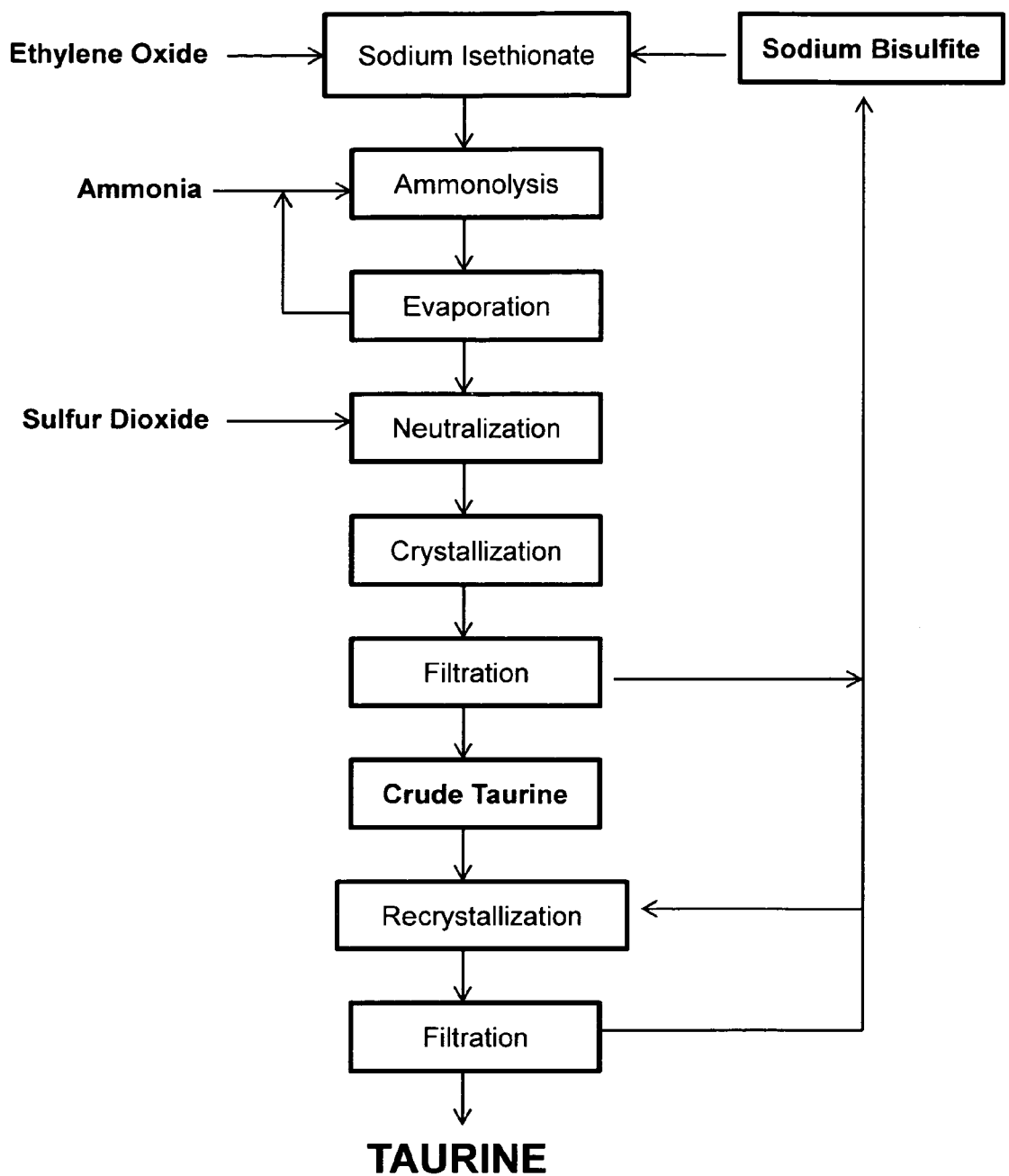

CYCLIC PROCESS FOR THE PRODUCTION OF TAURINE

TECHNICAL FIELD

This invention relates to a cyclic process for preparing taurine from ethylene oxide in high yield which is economical and in which little waste is generated.

DESCRIPTION OF THE INVENTION

Taurine can be referred to as 2-aminoethylsulfonic acid and is of the formula $H_2NCH_2CH_2SO_3H$. Taurine is an extremely useful compound because it per se has such pharmacological effects as detoxification effect, fatigue-relieving effect and nourishing and tonifying effect. As a result, taurine finds wide applications as an essential ingredient for human and animal nutrition.

Many chemical synthetic methods have been known in the prior arts for the preparation of taurine and related derivatives. The following two methods have been used in industry to manufacture over 50,000 tons of taurine per year, starting from ethylene oxide (the EO process) and monoethanolamine (the MEA process).

According to the EO process, EO is reacted with sodium bisulfite to obtain sodium isethionate, which undergoes ammonolysis to yield sodium taurinate. Neutralization with sulfuric acid results in a mixture of taurine and sodium sulfate.

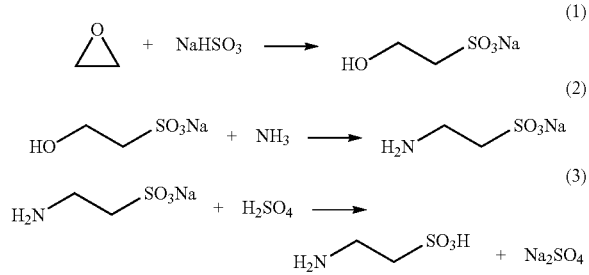

Starting from MEA, taurine can be prepared by reacting monoethanolamine with sulfuric acid to obtain the key intermediate, 2-aminoethyl hydrogen sulfate ester (AES). Subsequent reaction with sodium sulfite yields a mixture of taurine and sodium sulfate.

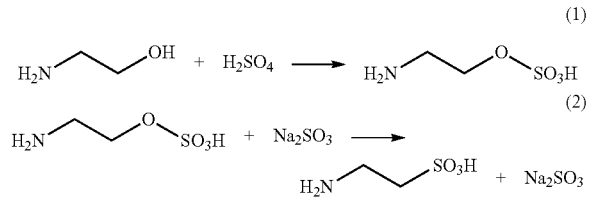

It is apparent from the reaction schemes that the final production stream comprises a mixture of taurine, sulfate salt, residual sulfite salt, and other impurities for both the EO and MEA processes. The content of inorganic salts alone is more than 50% of the total solid mass. To separate taurine from these salts, repeated crystallization at different temperature is required to produce a product of pharmaceutical grade that is suitable for human and animal consumption. The separation and purification steps are very complex, labor-intensive, and energy-intensive. Significant loss of taurine is also incurred during the final purification processing. The byproduct, sodium sulfate, is produced in large quantity, and is of low economic value and increasingly difficult to dispose of. As the yields for both processes are not very high (from 60 to 75%), a large quantity of waste, comprised of residual taurine, organic impurities, and inorganic salts, needs disposing of, and poses environmental pollutions.

It is an object of the present invention to overcome the disadvantage of the known process for the production of taurine and to provide, in addition, advantages, which will become apparent from the following description.

The process according to the present invention consists of reacting sulfur dioxide or sulfurous acid with the basic solution of taurinate, obtained in the EO process, at a temperature between 0° C. to 100° C., preferably between room temperature to 80° C., until the solution turns acidic to a pH from 3 to 7, more preferably 4-6. The cyclic process is schematically illustrated in the drawing and can be described by the following reactions:

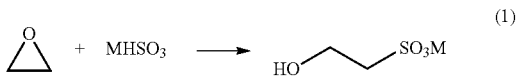

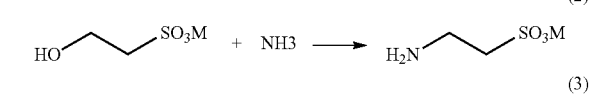

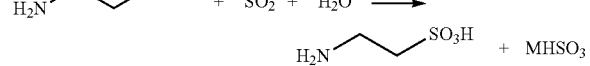

In the reactions, M stands for cations, which can be ammonium, lithium, sodium, and potassium.

The net reaction according to the present invention for the cyclic processes is:

The cyclic process starts from the reaction between EO and sodium bisulfite to produce sodium isethionate, i.e., sodium 2-hydroxyethylsulfonate, which undergoes ammonolysis to yield sodium taurinate. In comparison to the conventional process, acidification of the basic solution is effected with sulfur dioxide or sulfurous acid to yield taurine and to regenerate sodium bisulfite. After separating taurine by crystallization, the mother liquor that contains sodium bisulfite is recycled to the step for the reaction between EO and sodium bisulfite. No additional acid nor base foreign to the reaction system is introduced, thus salt formation is avoided.

The sulfur dioxide used may be pure or as sulfurous acid. However, it is also possible to use a product diluted by gases which are inert under reaction conditions, such as oxygen or nitrogen. In particular, there can be used the gases obtained from the combustion of sulfur or sulfur ore as produced in the manufacturing of sulfuric acid.

The process according to the present invention can be carried out discontinuously, semi-continuously, or continuously. The working pressure is usually atmospheric pressure. However, the reaction can also be carried out at a pressure above or below atmospheric pressure.

According to the process disclosed in the present invention, the reaction solution after neutralization consists of taurine and bisulfite salt, i.e. sodium bisulfite in the case where it is initially reacted with EO. After concentrating and cooling, taurine crystallizes out from the aqueous mixture.

After separating the precipitated taurine, the mother liquor comprised a small amount of residual taurine, unreacted starting materials, and sodium bisulfite or sulfite. This solution can be directly used to react with EO to produce sodium isethionate. The presence of taurine is not found to interfere with the reaction. An additional advantage is that taurine does not react with EO in the presence of a slight excess of sulfite salt.

On the other hand, the mother liquor can also be concentrated to crystallize sodium metabisulfite or sodium sulfite if impurities have accumulated in the mother liquor to the extent that the cyclic process is interfered. The recovered sodium metabisulfite, which is now free of impurities, can then be used to react with ethylene oxide to start the cyclic process.

The cyclic process according this invention can be further simplified by combining Step (3) and Step (1) in one step as described in the following reactions:

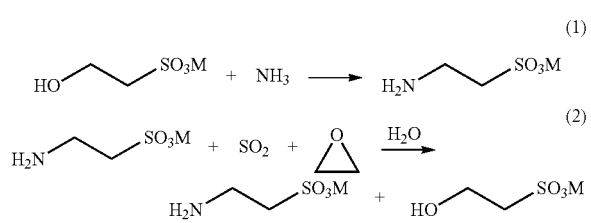

The resulting mixture is taurine and the starting material, 2-hydroxyethylsulfonate salt, which is also very soluble in water. Only taurine crystallizes from the solution.

In a further variation of the cyclic process according to the present invention, 2-hydroxyethyl sulfonic acid can be used as starting material, as described by the following reaction sequences:

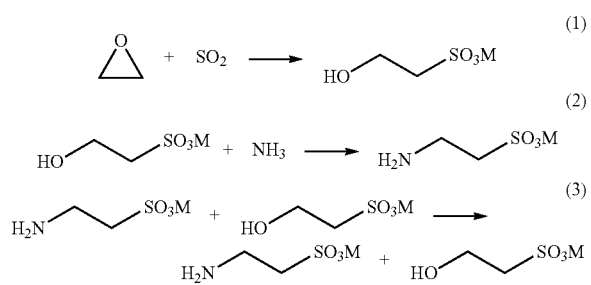

In this variation of the cyclic process, isethionic acid, which can be prepared first by reacting ethylene oxide with sulfur dioxide in by methods known in prior arts or obtained from other processes, is used an acid to neutralize the formed taurinate salt.

The advantage of the cyclic process according to the present invention in comparison to the known process is that no acid nor base, which is foreign to the reaction system, is used. Consequently, the cost of acid and base is completely avoided. In the previous known process, additional base, such as sodium hydroxide or ammonium hydroxide, is used to react with sulfur dioxide to produce a bisulfite salt for their subsequent reaction with EO, and then additional acid such as sulfuric acid is required to neutralize the resulted taurinate.

A particular advantage of the present process is the easiness that taurine can be separated and purified. In contrast to sodium sulfate, which shows similar and low solubility behavior to that of taurine at temperature below 40° C., both sodium bisulfite and sodium isethionate are quite soluble throughout the range of working temperature (0 to 100° C.) and does not crystallize from aqueous solution in the working concentration from 30 to 50% by weight. This large difference in solubility between taurine and other components in the reaction system such as sodium bisulfite or sodium isethionate renders their separation simple, efficient, and cost-effective. Upon concentrating and cooling, taurine crystallizes from aqueous solution, while sodium bisulfite or sodium isethionate remains in the solution. One additional recrystallization yields a final product of pharmaceutical grade.

DESCRIPTION OF THE DRAWING

The flowchart for preparing taurine from ethylene oxide, ammonia, and sulfur dioxide.

The following examples will illustrate the practice of this invention but are not intended to limit its scope.

EXAMPLE 1

44 g of ethylene oxide was reacted with a solution of 96 g of sodium metabisulfite to obtain a solution of sodium isethionate. The solution was then saturated with ammonia to about 25% and placed in a one liter autoclave and heated to 250° C. for 2 hours. After complete removal of ammonia from the solution, sulfur dioxide was bubbled in to neutralize the basic solution to pH 5-6. After concentrating and cooling, 110 g of crystalline taurine was obtained by filtration.

To the mother liquor was then added 40 g of ethylene oxide, followed by 500 mL of ammonium hydroxide (28%). After 2 hours at 250° C., evaporation and neutralization with sulfur dioxide, 108 g of taurine was obtained from the reaction solution.

Recrystallization from deionized water yields taurine of pharmaceutical grade.

EXAMPLE 2

The example was carried out in the same way as described in EXAMPLE 1, except that 2-hydroxyethylsulfonic acid is used, in place of sulfur dioxide, to neutralize the sodium taurinate. 102 g of taurine was obtained in the initial run and 104 g was obtained in the second run.

What is claimed is:
1. A cyclic process for the production of taurine, comprising:
   (a) reacting ethylene oxide with sodium bisulfite to form a reaction mixture comprising sodium isethionate;
   (b) adding ammonium hydroxide to the reaction mixture in (a) to prepare a reaction mixture comprising sodium taurinate;
   (c) removing ammonia and neutralizing the reaction mixture in (b) with sulfur dioxide or sulfurous acid to prepare a reaction mixture comprising taurine and regenerated sodium bisulfite and
   (d) recovering taurine from the reaction mixture in (c) and reacting the regenerated sodium bisulfite with ethylene oxide in (a).

2. The process of claim 1, wherein recovering taurine in step (d) comprises filtering the reaction mixture in (c) to recover taurine and concentrating the filtrate to recover sodium metabisulfite.

3. The process of claim 1, wherein recovering taurine in step (d) comprises crystallizing taurine.

\* \* \* \* \*

UNITED STATES PATENT AND TRADEMARK OFFICE
CERTIFICATE OF CORRECTION

PATENT NO. : 8,609,890 B1
APPLICATION NO. : 13/573076
DATED : December 17, 2013
INVENTOR(S) : Songzhou Hu It is certified that error appears in the above-identified patent and that said Letters Patent is hereby corrected as shown below:

On the Title Page

Item (60) Related U.S. Application Data should be,
Provisional application No. 61/573,117, filed on September 6, 2011.

Item (57) Abstract
change from "to regenerate sodium bisulfate" to --to regenerate sodium bisulfite--.

In the Specification

Column 1 should read,
--CROSS REFERENCE TO THE RELATED PATENT APPLICATION
This application claims the benefits of provisional application No. 61/573,117, filed on Sep. 6, 2011.--.

Column 3, Line 34 change from "  --.

Column 3, Line 45 change from " 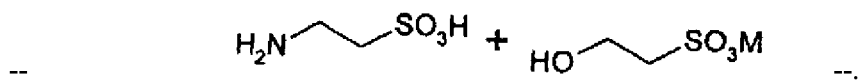 --.

Column 3, Line 50-54 should read,

Signed and Sealed this
Fourth Day of November, 2014

Michelle K. Lee
*Deputy Director of the United States Patent and Trademark Office*